United States Patent [19]

Packard et al.

[11] Patent Number: 5,824,968
[45] Date of Patent: Oct. 20, 1998

[54] EAR TIPS HAVING A PLURALITY OF EAR CONTACTING SURFACES

[75] Inventors: Thomas J. Packard; Mary Jo Rossini, both of St. Paul, Minn.

[73] Assignee: Minnesota Mining and Manufacturing Company, St. Paul, Minn.

[21] Appl. No.: 937,249

[22] Filed: Sep. 3, 1997

Related U.S. Application Data

[63] Continuation of Ser. No. 630,399, Apr. 10, 1996, abandoned.

[51] Int. Cl.$^6$ .................................................. A61B 7/02
[52] U.S. Cl. ........................................... 181/131; 181/135
[58] Field of Search ................................ 181/129, 130, 181/131, 135, 137; 381/69; 128/864, 867

[56] References Cited

U.S. PATENT DOCUMENTS

| | | | |
|---|---|---|---|
| 2,803,308 | 8/1957 | Di Mattia | 181/135 |
| 2,888,921 | 6/1959 | Nielson et al. | 128/865 |
| 2,934,160 | 4/1960 | TOUSON | 181/130 |
| 3,108,652 | 10/1963 | Littmann | 181/131 |
| 3,123,069 | 3/1964 | Laisne et al. | 120/865 |
| 3,275,099 | 9/1966 | Speelman | 181/131 |
| 3,303,902 | 2/1967 | Knott | 181/135 |
| 3,539,031 | 11/1970 | Scanlon | 181/23 |
| 3,618,600 | 11/1971 | Daoulas | 128/152 |
| 3,710,888 | 1/1973 | Peart | 181/24 |
| 3,732,382 | 5/1973 | DeWitt | 179/182 R |
| 3,736,929 | 6/1973 | Mills | 128/152 |
| 3,768,470 | 10/1973 | Leight | 128/152 |
| 3,881,570 | 5/1975 | Lewis | 181/135 |
| 3,882,848 | 5/1975 | Klar et al. | 122/2 Z |
| 3,895,627 | 7/1975 | Leight | 128/152 |
| 3,896,801 | 7/1975 | Grout | 128/152 |
| 3,935,401 | 1/1976 | Shore et al. | 179/182 R |
| 4,055,233 | 10/1977 | Huntress | 181/135 |
| 4,261,432 | 4/1981 | Gunterman | 181/131 |
| 4,434,794 | 3/1984 | Leight | 128/152 |
| 4,443,668 | 4/1984 | Warren | 179/156 |
| 4,540,063 | 9/1985 | Ochi | 181/135 |
| 4,564,009 | 1/1986 | Brinkhoff | 128/152 |
| 4,607,720 | 8/1986 | Hardt | 181/135 |
| 4,724,922 | 2/1988 | Kalayjian | 181/135 |
| 4,852,684 | 8/1989 | Packard | 181/131 |
| 4,870,689 | 9/1989 | Weiss | 381/68.6 |
| 4,913,259 | 4/1990 | Packard | 181/131 |
| 4,969,534 | 11/1990 | Kolpe et al. | 181/130 |
| 5,002,151 | 3/1991 | Oliveira et al. | 181/130 |
| 5,044,463 | 9/1991 | Carr | 181/135 |
| 5,046,580 | 9/1991 | Barton | 181/135 |
| 5,074,375 | 12/1991 | Grozil | 181/135 |
| 5,288,953 | 2/1994 | Peart | 181/130 |
| 5,449,865 | 9/1995 | Desnick et al. | 181/131 |
| 5,483,027 | 1/1996 | Krause | 181/135 |

FOREIGN PATENT DOCUMENTS

| | | |
|---|---|---|
| 2 310 741 | 5/1975 | France . |
| 154 516 | 7/1987 | Poland . |

OTHER PUBLICATIONS

Hal–Hen Company, Wholesale Net Price List, Long Island city, NY (No date).

Littmann Classic II Stethoscope; 3M Health Care, 3M Center Bldg. 275–4E–01, St. Paul, MN 55144–1000; 70–2008–3506–7 (12.75)ii. (No date).

Littmann Master Classic Stethoscope; 3M Health Care, 3M Center Bldg. 275–4E–01, St. Paul, MN 55144–1000; 70–2008–4251–9 (12.75)ii., (No date).

3M Littmann Master Cardiology Stethoscope; 3M Health Care, 3M Center, Bldg. 275–4E–01, St. Paul, Minnesota (No date).

3M Littmann Cardiology Stethoscope; 3M Health Care, 3M Center Bldg. 275–4E–01, St. Paul, MN 55144–1000; 70–2008–3507–5 (141.5)ii. (No date).

*Primary Examiner*—Eddie C. Lee
*Attorney, Agent, or Firm*—Gary L. Griswold; Jeffrey J. Hohenshell

[57] ABSTRACT

An ear tip having a central portion and two end portions is described. The end portions each have ear contacting surfaces that are sized and shaped to contact the ear of the user. The ear tips are easily cleaned. The ear tips also contribute to user comfort and convenience.

16 Claims, 5 Drawing Sheets

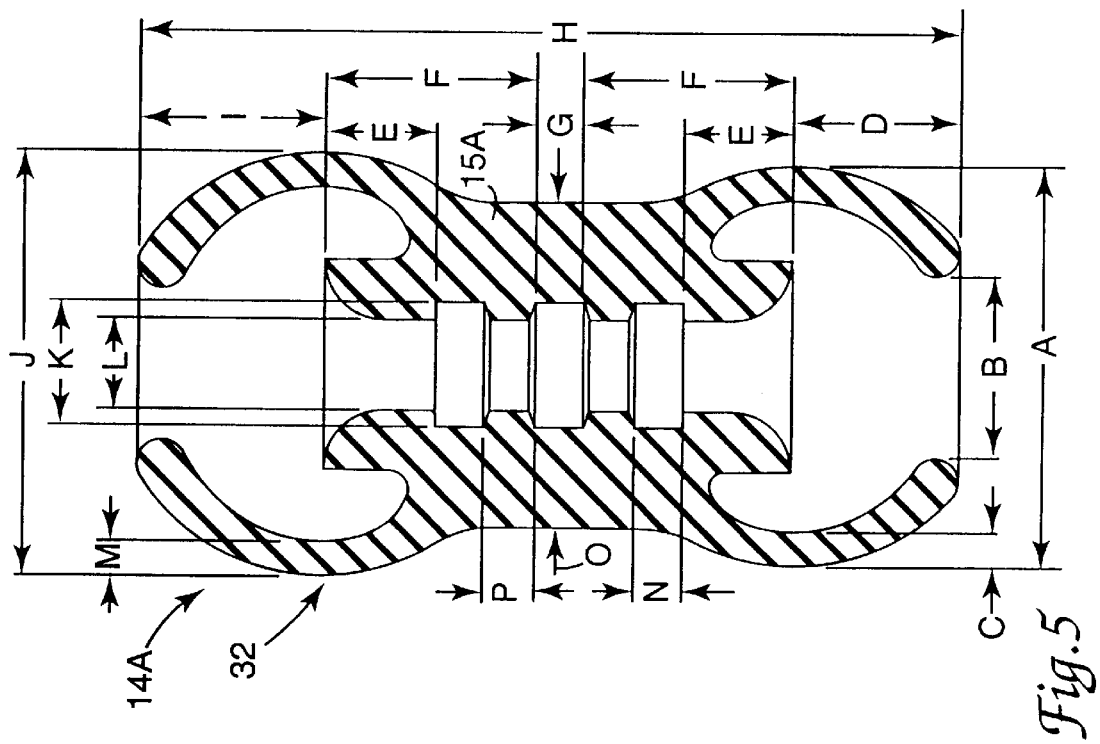
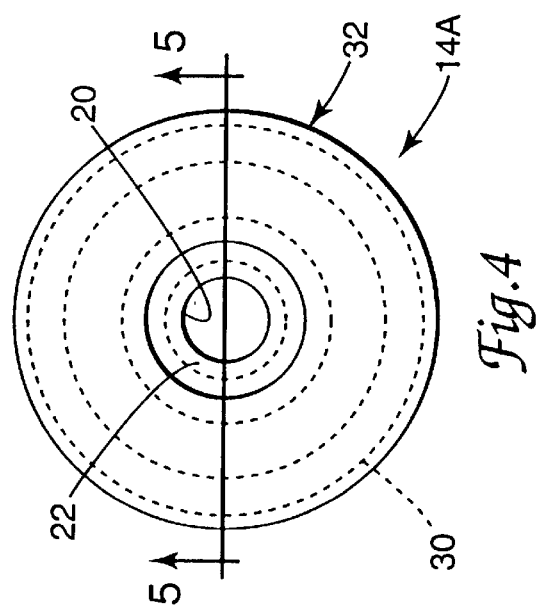

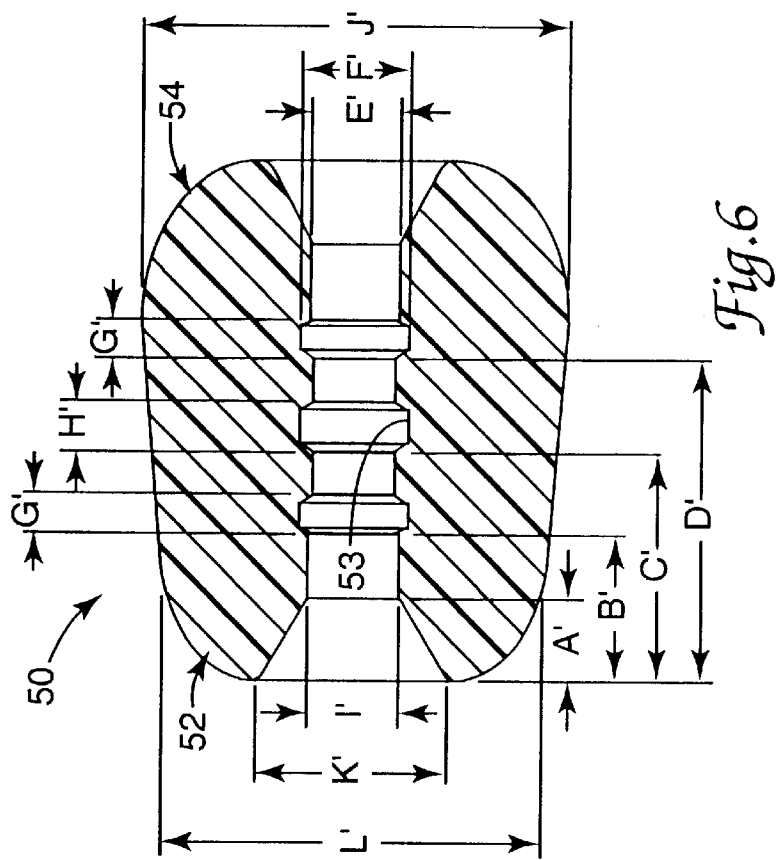
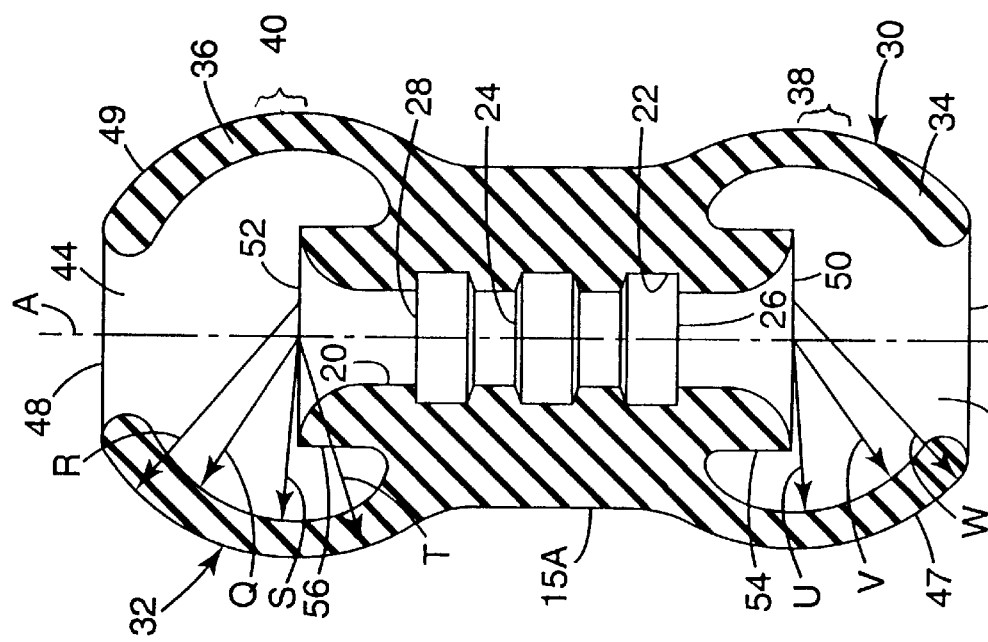

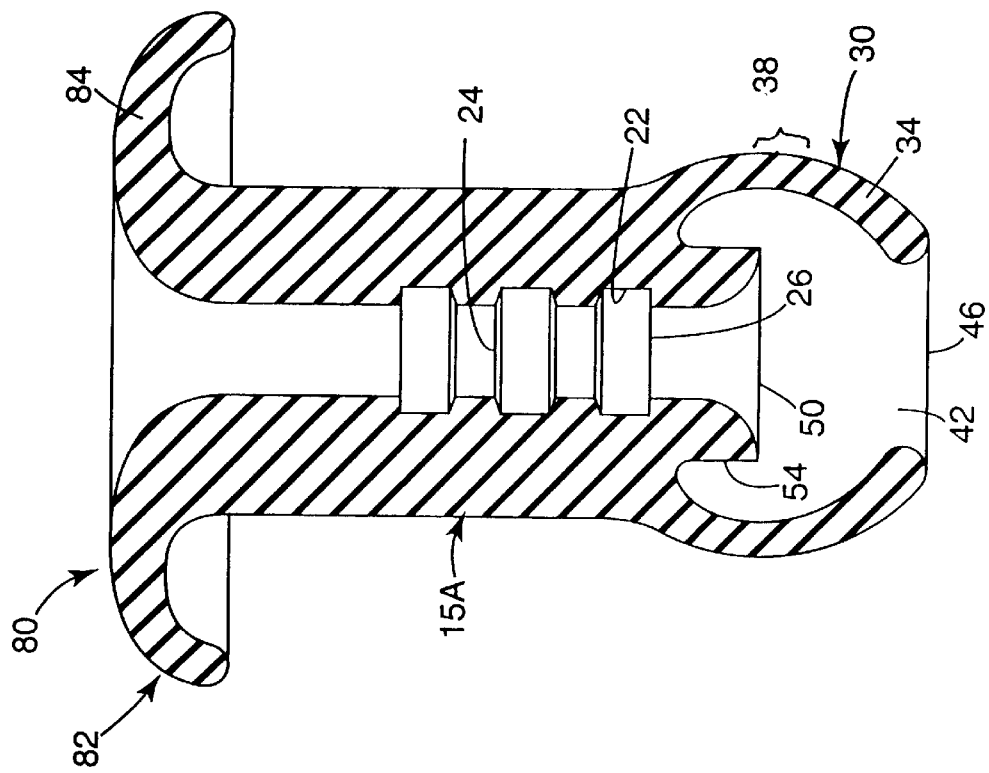
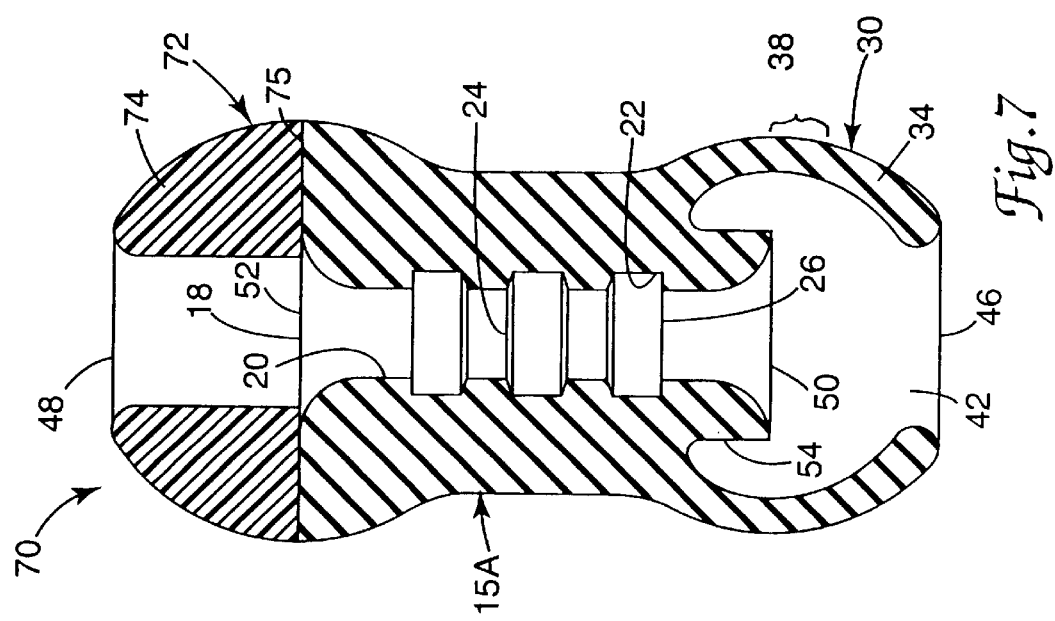

EAR TIPS HAVING A PLURALITY OF EAR CONTACTING SURFACES

This is a continuation of application Ser. No. 08/630,399 filed Apr. 10, 1996, now abandoned.

TECHNICAL FIELD

This invention relates to ear tips for adapting stethoscopes to the human ear, and more particularly to ear tips which include a plurality of contacting surfaces to suit the preference of the user.

BACKGROUND

The stethoscope is an important part of medical diagnostics. Commercial embodiments of medical diagnostic stethoscopes include the 3M Littmann™ Master Cardiology and the 3M Littmann™ Cardiology II stethoscopes sold more than one year prior to the filing date of the present application by Minnesota Mining and Manufacturing Co. (3M) of St. Paul, Minn.

Stethoscopes include ear tips for contacting the ears of the user and biasing mechanisms for forcing the ear tips against the user's ears in an effort to create an acoustic seal that helps the stethoscope convey only the desired sounds free of ambient interference. The art of ear tips for stethoscopes is replete with various types, sizes and shapes of ear tips, due at least in part to a desire to provide a comfortable ear tip that provides an acoustic seal between the ear tip and the ear. Vendors typically sell stethoscopes with a plurality of discrete, individual types, shapes or sizes of ear tips to satisfy the individual preference of the stethoscope user.

A variety of factors make the design of a stethoscope ear tip a particularly difficult challenge. For many persons, the exterior auditory canal is sensitive to pressure. During use of some stethoscopes, the ear tip tends to be twisted against the sensitive external auditory canal. This tends to cause irritation resulting in an ear tip that is perceived as being uncomfortable. An individual's internal auditory canal is typically even more sensitive than the exterior auditory canal, and thus, the internal auditory canal is even more prone to becoming irritated.

While user comfort and fit are important considerations for an ear tip, the ear tip should also provide an appropriate acoustic seal. Even a small amount of ambient interference may seriously adversely affect the sound transmission characteristics of a stethoscope. For example, small acoustic leaks at the ear tip/ear interface may be seriously detrimental to overall acoustic power and quality transmission.

The external and internal structures of the ear vary in size and shape from person to person. Even the exterior auditory meatus on the opposite sides of an individual's head may vary considerably. The vagaries associated with the human ear present a particularly difficult challenge to the ear tip art.

Stethoscope manufacturers typically inventory two or more sizes of ear tips to suit the user's preference. Additionally, the art also developed several different types and shapes of ear tips from which consumers may choose. For example, U.S. Pat. Nos. 4,852,684; 4,913,259; 5,288,953; and 5,449,865 describe ear tips that may be constructed from an elastomeric material to provide an ear tip which is perceived as soft by the user. In contrast, some users prefer an ear tip which is constructed from a relatively firm material such as an acetal resin (e.g. Delrin available from DuPont). Other users prefer an ear tip which is constructed in the easy to manufacture mushroom shape. A mushroom shaped ear tip is described in U.S. Pat. No. 3,710,888 (the entire contents of which is herein incorporated by reference). Other ear tips are disclosed in U.S. Pat. Nos. 2,803,308 and 3,108,652 and Poland Patent Specification No. 154 516 to Andrzej Krzysztof.

It is also important to maintain clean ear tips in order to resist the transmission of disease and to maintain the desired acoustic properties of the stethoscope. Typically ear tips are mounted to the stethoscope with structure that allows them to be manually removed from the stethoscope, cleaned, and then replaced on the stethoscope. The structure also affords replacement of an ear tip with a new ear tip should the ear tip become damaged, dirty or excessively worn. However, when the replacement ear tip or the cleaning facilities are located in a remote location, prior art ear tips do not provide a readily available, clean ear tip.

SUMMARY OF THE INVENTION

The present invention comprises an ear tip for use with a stethoscope to transmit sound to a human ear. The novel ear tip includes a plurality of ear contacting surfaces which may optionally differ in size, shape and type. The present invention provides ear tips which: a) afford clean, hygienic ear contacting surfaces for the user, b) optionally afford a plurality of types, shapes or sizes of ear contacting surfaces to suit user preferences or requirements, c) increase the capacity of the stethoscope to provide a desired acoustic seal with the user's ear. In addition, cost is potentially reduced, as the need to purchase a plurality of ear tips in order to obtain the desired shapes, sizes or types is eliminated.

Stethoscopes which utilize the ear tips of the present invention have a pair of sound-transmitting members with distal ends. An ear tip comprises a central portion that has an attachment means or structure for attaching the ear tip to a distal end of a sound-transmitting member of the stethoscope.

The ear tip has first and second end portions that are adapted to be in acoustic communication with the central portion. Preferably, the first and second end portions are on opposite sides of the central portion. The first and second end portions have surfaces defining outlets, and ear contacting surfaces that are sized and shaped to afford engagement with the ear. The central portion and first and second end portions also have inner surfaces defining a sound transmitting conduit extending between the outlets of the first and second end portions. The conduit is sized and shaped to afford passage of the desired sound (e.g. heart and lung sounds).

The attachment means affords releasable connection of the ear tip to the sound-transmitting member of the stethoscope in either of: a) a first orientation in which the ear contacting surfaces of the first end portion are positioned relative to the stethoscope to engage the ear, and the ear contacting surfaces of the second end portion are spaced from the ear; or b) a second orientation in which the ear contacting surfaces of the second end portion are positioned relative to the stethoscope to engage the ear, and the ear contacting surfaces of the first end portion are spaced from the ear. Preferably, in the first orientation, the distal end of the sound transmitting member is passed through the outlet of the second end portion and into the central portion of the ear tip.

In one embodiment, the first end portion is substantially identical to the second end portion. Optionally, the size, shape or type of the first and second end portions may vary.

As used herein, when it is said that the first end portion of the ear tip is of a substantially different size than the second end portion of the ear tip, it is meant that the physical dimensions, proportions, magnitude or extent of the first end portion is different than the physical dimensions, proportions, magnitude or extent of the second end portion. Ear tips having first and second end portions of different sizes accommodate persons with varying ear sizes and may reduce the need to inventory several different sizes of ear tips.

In this application, when it is said that the first end portion of the ear tip is of substantially the same shape as the second end portion of the ear tip, it is meant that the characteristic surface configuration of the first and second end portions are substantially identical without taking into consideration the relative sizes of the first and second end portions. Examples of different shapes of end portions include bulbous, mushroom and spherical shaped end portions. Ear tips with first and second end portions with different shapes afford a user the choice between different shapes of surfaces for contacting the ear and may help tailor the ear tips for the particular needs and/or preferences of a user.

When the present application states that the first end portion of the ear tip is of a different type than the second end portion of the ear tip, it is meant that the first end portion and the second end portion do not share common traits or characteristics that distinguish them as an identifiable group or class. For example, consider an ear tip having first and second end portions which have a common size and shape but which include one end portion constructed from a relatively firm material and the other end portion constructed from a less firm material. Even though the end portions may have substantially the same shape and substantially the same size, one end portion may be perceived as soft by the user while the other end portion may be perceived as being hard. That ear tip has a first end portion that is of a different type than the second end portion of the ear tip.

Another example of an ear tip having first and second end portions of different types comprises an ear tip with the ear contacting surfaces of the second end portion sized and shaped to engage the interior surfaces of the auditory canal of the ear, and with the ear contacting surfaces of the first end portion sized and shaped to contact the external acoustic meatus of the exterior of the auditory canal. Preferably, the first end portion is deformable under forces typically encountered during use of a stethoscope and the ear contacting surfaces of the second end portion are sized and shaped so that it may be positioned in the interior portion of the concha behind the tragus over the auditory canal orifice.

Ear tips with different types of first and second end portions afford a user the choice between different types of surfaces for contacting the ear and may help tailor the ear tips to the user's particular needs or preferences.

BRIEF DESCRIPTION OF THE DRAWINGS

The present invention will be further described with reference to the accompanying drawing wherein like reference numeral refer to like parts in the several views, and wherein:

FIG. 4 is an end view of a second embodiment of ear tip according to the present invention with dashed lines illustrating hidden details of the ear tip;

FIG. 5 is a cross section view of the ear tip of FIG. 4 taken approximately along lines 5—5 of FIG. 4;

FIG. 5A is an another version of the cross section view of FIG. 5 with additional reference characters emphasizing different details than those of FIG. 5;

FIG. 6 is a cross section of a third embodiment of ear tip according to the present invention;

FIG. 7 is a cross section of a fourth embodiment of ear tip according to the present invention;

FIG. 8 is a cross section of a fifth embodiment of ear tip according to the present invention;

DETAILED DESCRIPTION

Figure 1:
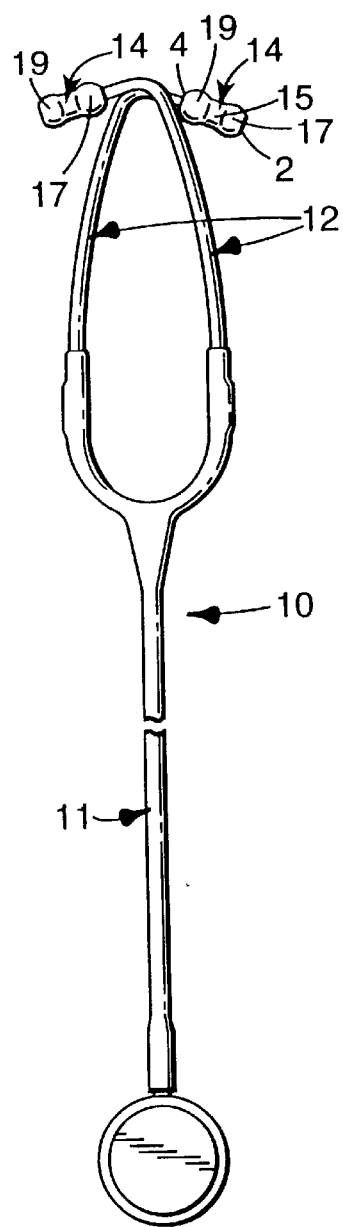
FIG. 1 is a plan view of a stethoscope having a pair of sound transmitting members and a pair of ear tips according to a first embodiment of the present invention.

Referring now to FIG. 1, there is shown a spring loaded stethoscope 10 having a pair of ear tips 14 according to the present invention. It should be noted that the ear tips 14 are suitable for use with a wide variety of stethoscopes used in medical diagnostic procedures. Examples of suitable stethoscopes for use with the ear tips 14 include the stethoscopes disclosed in U.S. Pat. Nos. 3,108,652; 3,152,659; 3,168,160; 3,168,161; 3,276,536; 3,366,198; 3,504,760; 4,200,269; 4,440,258; 4,475,619 and 5,111,904 (the entire contents of each of which are herein incorporated by reference). Particular examples of stethoscopes include the 3M Littmann™ Master Cardiology and the 3M Littmann™ Cardiology II stethoscopes sold by Minnesota Mining and Manufacturing Co. (3M) of St. Paul, Minn.

Figure 2:
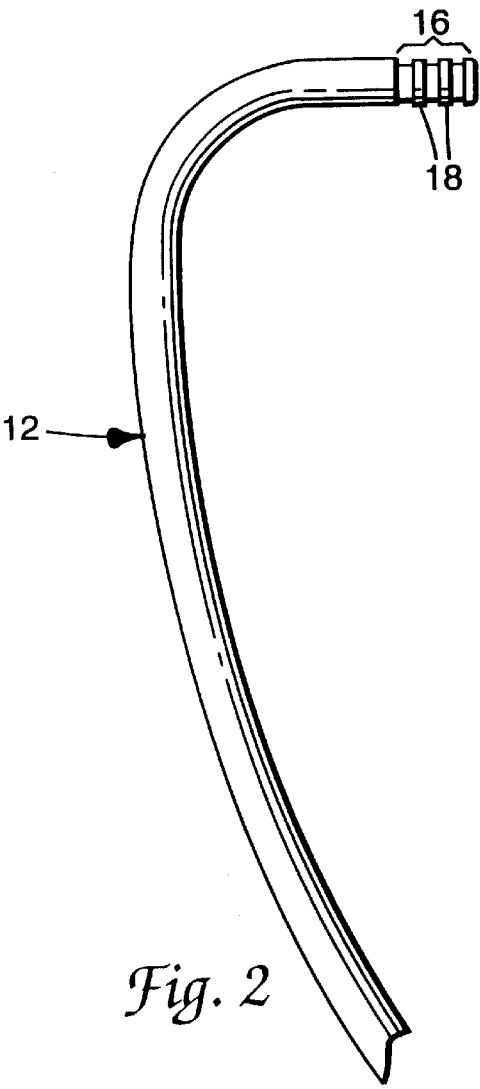
FIG. 2 is an enlarged detail plan view of a portion of one of the sound transmitting members of the stethoscope of FIG. 1 with its ear tip removed.

A preferred stethoscope has a binaural 11 with dual, hollow, sound transmitting tubes 12 terminating in the ear tips 14. As used herein, the term "binaural" means all portions of the stethoscope other than the chestpiece and the ear tips. FIG. 2 illustrates a detail plan view of one of the sound transmitting tubes 12 of the stethoscope 10 of FIG. 1 with its ear tip 14 removed for clarity.

Figure 3:
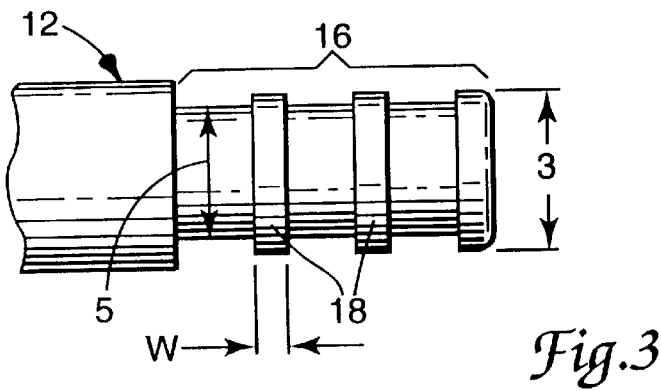
FIG. 3 is an enlarged detail plan view of the distal end of the sound transmitting member of FIG. 2.

The ear tip connection or distal end 16 of the sound transmitting tube 12 is shown in detail in FIG. 3. The ear tip connection end 16 typically has one or more flanges 18. The sound transmitting tubes 12 may be fabricated from any suitable materials, with hardened aluminum, brass or stainless steel being considered particularly preferred. However, other suitable plastic or metal materials may optionally be employed.

In a preferred embodiment, the distal ends 16 of the sound transmitting tubes 12 have a maximum outer diameter 5 (FIG. 3) and the flanges define a maximum flange diameter 3 (FIG. 3) and a width W. Also preferably, the attachment section 16 is about 0.4 inches in length.

Figure 9:
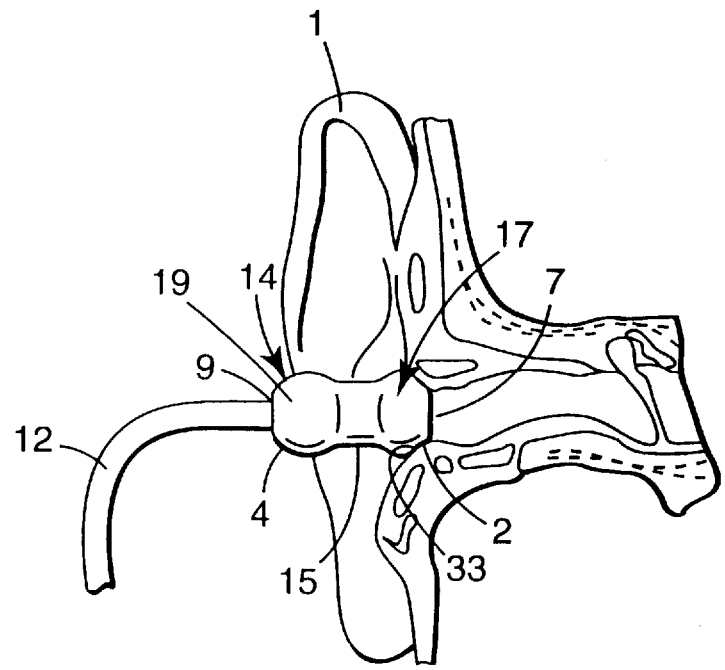
FIG. 9 is a plan view of the ear tip of FIG. 1 shown in its compressed state in the ear.

Referring now to FIGS. 1 and 9, there is shown a first embodiment of ear tip 14 according to the present invention. The ear tip 14 comprises a central portion 15 having an attachment means for attaching the ear tip to the distal end 16 of the sound-transmitting members 12 of the stethoscope 10. The attachment means is described in greater detail below.

The ear tip 14 includes a first end portion 17 in acoustic communication with the central portion 15 and surfaces defining an outlet 7. The first end portion 17 has ear contacting surfaces 2 that are sized and shaped to afford engagement with the ear 1. The ear tip 14 also has a second end portion 19 opposite the first end portion 17. The second end portion 19 is also adapted to be placed in acoustic communication with the central portion 15, but, in the orientation shown in FIG. 9, the second end portion 19 is not in acoustic communication with the central portion 15.

The second end portion 19 has surfaces defining an outlet 9 and ear contacting surfaces 4 that are sized and shaped to afford engagement with the ear 1. The central portion 15, and first and second end portions 17 and 19 also have inner surfaces defining a sound transmitting conduit extending between the outlets 7 and 9. The conduit is sized and shaped to afford passage of sound.

The attachment means within the central portion 15 affords releasable connection of the ear tip 14 to the sound-transmitting member 12 of the stethoscope 10 in either of: a) a first orientation (FIG. 9) in which the ear contacting surfaces 2 of the first end portion 17 are positioned relative to the stethoscope 10 to engage the ear 1, and the ear contacting surfaces 4 of the second end portion 19 are spaced from the ear; or b) a second orientation in which the ear contacting surfaces 4 of the second end portion 19 are positioned relative to the stethoscope 10 to engage the ear 1, and the ear contacting surfaces 2 of the first end portion 17 are spaced from the ear 1 (compare the orientations of the two ear tips in FIG. 1).

The ear tip 14 shown in FIGS. 1 and 9 includes first and second end portions 17 and 19 that are substantially identical in size, shape and type. The ear tip 14 is preferably constructed from a single uniform, soft material. For example, the end portions 17 and 19 may each comprise the second sections of the ear tips described in U.S. Pat. Nos. 4,852,684 and 4,913,259 (the entire contents of each of which are herein incorporated by reference). As another example, the end portions 17 and 19 may each comprise the outer body member of the ear tips described in U.S. Pat. Nos. 5,288,953 or 5,449,865 (the entire contents of each are herein incorporated by reference) which provide an ear tip which is perceived as soft by users. Alternatively, the end portions 17 and 19 may be constructed from a relatively firm material.

Preferably, the attachment means of the ear tips 14 comprises a plurality of ribs and grooves which fit into corresponding complementary ribs or flanges 18 and grooves on the distal ends 16 of the sound-transmitting members 12. For example, the attachment means for the ear tips 14 may comprise the attachment means substantially as described in U.S. Pat. No. 5,449,865. Alternatively the attachment means may comprise a threaded portion (not shown) that allows the ear tip 14 to be screwed onto a distal end 16 of a sound transmitting member 12 that is correspondingly threaded. This type of attachment means may be particularly preferred if the ear tip is constructed from a relatively firm material, as the threads may be formed in the firm material itself. Alternatively, the threaded portion may be provided by a threaded metal element inserted into the central portion 15 (particularly if the ear tip is constructed from a relatively flexible material), or the threads may be simply molded into the central portion. Yet another alternative structure which may comprise the attachment means is a simple friction fit or interference fit between the distal end of the sound transmitting tube and the central portion of the ear tip.

As shown in FIG. 9, in the first orientation, the distal end of the sound transmitting member 12 is passed through the outlet (e.g. 9) of one of the end portions (e.g. 19) and into the central portion (e.g. 15) of the ear tip 14. The sound transmitting conduit within the ear tip 14 should be sized and shaped to afford passage of the distal end of the sound transmitting member 12 when the ear tip is in either of the first and second orientations. Alternatively, the ear tip could be flexible to allow the sound transmitting tube to pass through the outlet of the end portion that is spaced from the ear, through a portion of the interior conduit and into the attachment means.

The attachment means allows the user to choose between the ear contacting surfaces 2 or 4 of the first and second end portions 17 and 19. For example, with use, the first end portion 17 may become excessively worn or dirty. The attachment means allows the ear tip 14 to be used in an orientation that spaces the worn or dirty first end portion 17 from the ear 1 while the desired ear contacting surfaces 4 of the second end portion 19 actually contact the ear 1.

A second embodiment of ear tip 14A according to the present invention is illustrated in FIGS. 4, 5 and 5A in a relaxed or non-compressed state. The ear tip 14A comprises a central portion 15A that has an attachment means for attaching the ear tip 14A to a distal end 16 of a sound-transmitting member 12 of a stethoscope 10.

The ear tip has first 30 and second 32 end portions that are adapted to be placed in acoustic communication with the central portion 15A. The first and second end portions 30 and 32 have surfaces defining outlets 46 and 48, and ear contacting surfaces 47 and 49 that are sized and shaped to afford engagement with the ear 1. The central portion 15A and end portions 30 and 32 also have inner surfaces defining a sound transmitting conduit 20 extending between the outlets 46 and 48 of the end portions 30 and 32.

While the first and second end portions 30 and 32 are of substantially the same general shape (e.g. bulbous) and type (e.g. substantially the entire ear tip is constructed from a uniform, soft elastomeric material), the second end portion 32 is slightly larger than the first end portion 30. Referring to FIG. 5A, the first and second end portions 30 and 32 have walls 34 and 36 having a region of greatest outside diameter 38 and 40. The walls 34 and 36 define hollow inner chambers 42 and 44 in open communication with outlets 46 and 48 and adapted to be placed in open acoustic communication with the ear's auditory canal. Preferably, the greatest outside diameter of the first end portion 30 is different than the greatest outside diameter of the second end portion 32.

The walls 34 and 36 of the end portions 30 and 32 are relatively thin throughout, such that the ratio of (i) the inside diameter of the end portion measured at the point of greatest outside diameter of that end portion to (ii) the greatest outside diameter of that end portion is between about 0.6 and 0.95 and preferably between about 0.8 and 0.95. Preferably, the walls 34 and 36 extend from their junction with the walls of the central portion 15A outwardly for a distance and then inwardly thereafter with reference to the axis A in a smooth, continuously curved, symmetrical fashion to provide an example of a bulbous shaped end portion with an inner surface that is convex relative to the inside of the hollow chamber (42 or 44). As seen in FIGS. 5 and 5A, the walls 34 and 36 define the hollow inner chamber (42 or 44). The thickness of the walls 34 and 36 may vary, but the thickness of the walls is preferably at a minimum in the region of greatest outside diameter (38 and 40) of their respective end portion. This preferred embodiment allows the end portions 30 and 32 to deform in the region of minimum thickness under the pressures exerted by the spring-loaded stethoscope, causing the end portion to bulge outwardly.

The ear tip 14A is placed in a compressed state upon being forced against the external acoustic meatus 33 of the human ear by pressure exerted through sound transmitting tubes 12 of the stethoscope 10 in a manner similar to that of the first embodiment of ear tip 14 shown in FIG. 9. The ear tip 14A is not intended to penetrate deeply into the ear canal. Instead, walls 34 or 36 deform and preferably bulge presenting a relatively large surface contact area to the external acoustic meatus 33. In this manner, the ear contacting surfaces 47 or 49 may conform closely to the irregular surfaces of the external acoustic meatus 33 resulting in a comfortable ear tip which nevertheless excludes sufficient ambient noise to provide an acceptable conduit for sounds transmitted through tubes 12.

An ear tip with varying sizes of first and second end portions may accommodate the very wide range of common ear canal sizes. The maximum outside diameter of the first and second end portions 30 and 32 in a relaxed state should be at least about 0.4 inches to resist penetration of the ear tip into the ear canal, and less than about 0.6 inches to assure that the ear tip will fit the ear. This range is preferred for an ear tip constructed from a flexible, resilient material designed to allow the ear contacting surfaces 47 and 49 to expand about the external acoustic meatus of the ear 1.

The attachment means for the ear tip 14A may comprise a plurality of molded-in recesses 22. Some of the edges 24 of the recesses 22 are tapered to allow easy insertion of the distal ends 16 of the sound transmitting tubes 12. Edges 26 and 28 are preferably left square relative to the axis A of the ear tip 14A to resist the inadvertent protrusion of the distal end 16 of the sound transmitting tube 12 into the ear of the user. All of the recesses 22 are sized and shaped to engage the flanges 18 on sound transmitting tubes 12 in a complementary fashion.

The attachment means of the ear tip 14A affords releasable connection of the ear tip 14A to the sound-transmitting member 12 of the stethoscope 10 in a first orientation in which the ear contacting surfaces 47 of the smaller first end portion 30 are positioned relative to the stethoscope 10 to engage the external acoustic meatus of the ear 1, and the ear contacting surfaces 49 of the second end portion 32 are spaced from the ear. Users with a relatively small external acoustic meatus and/or auditory canal may prefer to use the ear tip 14A in this first orientation. The attachment means also affords releasable connection of the ear tip 14A to the sound-transmitting member 12 of the stethoscope 10 in a second orientation in which the ear contacting surfaces 49 of the larger second end portion 32 are positioned relative to the stethoscope 10 to engage the external acoustic meatus of the ear 1 and the ear contacting surfaces 47 of the first end portion 30 are spaced from the ear 1. Stethoscope users with a relatively large external acoustic meatus and/or auditory canal may prefer to use the ear tip 14A in this second orientation.

Chambers 42 and 44 each include an entry port 50 and 52 defined by short cylindrical stops 54 and 56 which project into the chambers 42 and 44 a predetermined distance to provide a stop means to prevent extensive inward compression of walls 34 and 36 respectively (and potentially a collapse of the ear tip), but which afford enough compression of walls 34 and 36 to allow the ear tip 14A to conform to the external acoustic meatus of the ear. Preferably, the structures defining entry ports 50 and 52 do not extend to outlets 46 and 48 in order to provide the desired compression of the ear tip 14A.

The ear tip 14A is preferably formed of a flexible, resilient material such as a non-porous elastomeric material. Ear tips 14A should be constructed of a material which is compatible with contact with the human ear. Compatibility in this sense includes both resistance to the acidic oils present in the ear as well as low cytotoxicity. Suitable materials include vulcanized natural rubber, vinyl elastomers, elastomeric polyurethanes (see e.g. U.S. Pat. No. 5,449,865), silicone elastomers or rubbers (see e.g. U.S. Pat. No. 5,449,865), nitrile rubbers, and thermoplastic rubbers (see e.g. U.S. Pat. No. 5,449,865).

An appropriate hardness is also important for providing comfort to the user of the stethoscope. Preferably, the hardness of the ear tip 14A should be between about 30 and 80 Shore A, and more preferably between about 40 and 50 Shore A. Most preferably, the hardness should be about 45 Shore A. The harder the material, the thinner the wall 34 or 36 should be in order for the ear tip to compress and spread properly under the load of the stethoscope. The lower limit of Shore hardness is that which prevents the forces provided by a stethoscope from collapsing the end portion in such a fashion that open communication between the end portion and the ear canal is blocked.

The ear tip 14A may be constructed by a variety of conventional methods including compression molding, transfer molding, liquid casting, and injection molding.

EXAMPLE 1

An ear tip 14A may be used with any of the examples of sound transmitting tubes found in U.S. Pat. No. 5,449,865 to Desnick et al.

An ear tip according to the present invention with the shape shown in FIGS. 5 and 5A preferably has the dimensions as shown in Table A. The ear tip is preferably constructed entirely of a silicone elastomer (rubber). The ear tip preferably has a Shore A hardness value of 45 A plus or minus 5. The Shore hardness values are determined by ASTM D 2240-86 and values are read after 3 seconds.

TABLE A

| Dimension | Approximate Length (inches) |
| --- | --- |
| A | 0.48 |
| B | 0.20 |
| C | 0.04 |
| D | 0.22 |
| E | 0.14 |
| F | 0.27 |
| G | 0.06 |
| H | 1.07 |
| I | 0.25 |
| J | 0.52 |
| K | 0.15 |
| L | 0.1 |
| M | 0.04 |
| N | 0.05 |
| O | 0.38 |
| P | 0.08 |
| Q | 0.22 |
| R | 0.32 |
| S | 0.13 |
| T | 0.26 |
| U | 0.15 |
| V | 0.2 |
| W | 0.29 |

The thickness of the walls 34 and 36, the hardness of the walls 34 and 36, the wall geometry, and the wall materials are chosen such that the forces caused by the stethoscope do not cause the ear tip 14A to collapse or fold along the axis A, but yet provides a flexible, resilient ear tip that is perceived as comfortable by many users. The walls 34 and 36 are sized, shaped and constructed to avoid folding over the axis A of the ear tip 14A under normal stethoscope loading conditions with attendant loss of open acoustic communication between the ear and stethoscope 10. Proper performance of the ear tip 14A is also affected by internal dimensions.

FIG. 6 illustrates a cross section view of an alternate embodiment of an ear tip 50. The outer surfaces of the ear tip 50 are preferably substantially frustum or frusto-conical shaped. In particular, the outer surfaces are the conical section of a cone between two parallel planes cutting the cone perpendicular to the axis of the cone.

The ear tip 50 includes a first end portion 52, a second end portion 54 and a central portion 53. Table B sets forth suitable dimensions for an ear tip 50:

TABLE B

| Dimension | Approximate Length (inches) |
| --- | --- |
| A' | 0.10 |
| B' | 0.18 |
| C' | 0.29 |
| D' | 0.40 |
| E' | 0.11 |
| F' | 0.14 |
| G' | 0.05 |
| H' | 0.06 |
| I' | 0.11 |
| J' | 0.53 |
| K' | 0.2 |
| L' | 0.48 |

The ear tip 50 may be constructed from a relatively firm material that results in an eartip that is perceived as being relatively hard by the user. An ear tip 50 constructed from a relatively firm material is inflexible under normal loading conditions created by a stethoscope with a biasing mechanism. As used in this application, the hardness of a relatively firm material should be between about 50 and 90 on the Shore A scale. Even though a relatively firm material is used for the ear tip 50, the attachment means may nevertheless comprise complimentary ribs and grooves.

FIG. 7 illustrates another embodiment of ear tip according to the present invention generally designated by reference character 70. The ear tip 70 has a first end portion 30 and a central portion 15A that are substantially identical with the first end portion and central portion of the ear tip 14A described above with like reference characters in FIGS. 5, 5A and 7 referring to substantially identical parts.

Unlike the ear tip 14A, the walls 74 of the second portion 72 of the ear tip 70 have a different shape than the walls of the first end portion 30. The walls 74 may be constructed from a relatively firm or a relatively elastomeric material, but the second end portion 72 will be perceived as providing a relatively hard ear tip, primarily due to the increased thickness of the walls 74 compared with the walls 34.

The material forming the walls 74 may be the same or a different material than the material forming the walls 34. For example, the material forming the walls 74 may comprise a relatively firm material when compared with the material forming the walls 34 or vice versa. The material forming the walls 74 may be adhered to the material of the rest of the ear tip with an adhesive 75.

FIG. 8 illustrates another embodiment of ear tip according to the present invention generally designated by reference character 80. The ear tip 80 has a first end portion 30 and a central portion 15A that are substantially identical with the first end portion and central portion of the ear tip 14A described above with like reference characters in FIGS. 5, 5A and 8 referring to substantially identical parts.

Unlike the ear tip 14A, the walls 84 of the second end portion 82 of the ear tip 80 form a generally mushroom shaped second end portion 82. For example, the second end portion 82 of the ear tip 80 may comprise the second end portion of the mushroom shaped ear tip illustrated in FIG. 2 of U.S. Pat. No. 3,710,888 and described therein (the entire contents of which are incorporated by reference).

Figure 10:
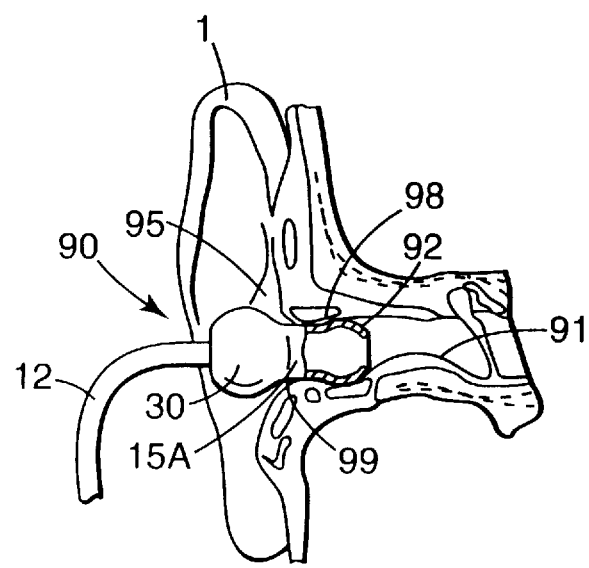
FIG. 10 is a plan view of an sixth embodiment of ear tip according to the present invention shown with an end portion inserted into the auditory canal of the user.

FIG. 10 illustrates another embodiment of ear tip according to the present invention generally designated by reference character 90. The first end portion 30 and central portion 15A of the ear tip 90 are substantially identical to the first end portion and central portion of the ear tip 14A illustrated in FIGS. 5 and 5A and described above. The second end portion 92 of the ear tip 90, however, is of a different size, type and shape when compared to the first end portion 30.

FIG. 10 schematically illustrates generally ear anatomy. The ear 1 includes the concha 95, tragus 98 and anti-tragus 99. Ear contacting surfaces of the second end portion 92 are sized and shaped to engage the interior surfaces of the auditory canal 91 of the ear, as opposed to the ear contacting surfaces of the first end portion 30 which are sized and shaped to contact the external acoustic meatus 33 (see FIG. 9) of the exterior of the auditory canal. Preferably, the ear contacting surfaces of the second end portion 92 are designed to be positioned in the interior portion of the concha 95 behind the tragus 98 over the auditory canal orifice. The second end portion 92 is preferably generally spherical shaped as opposed to the substantially bulbous shape of the first end portion 30. Generally, the first end portion 30 is larger in maximum outer diameter than the second end portion 92. Of course the first end portion 30 is of a different type than the second end portion 92. As an example, the second end portion may be constructed according to the disclosure of the ear piece in U.S. Pat. No. 3,732,382 (the entire contents of which are herein incorporated by reference). The ear tip 90 may help tailor the stethoscope for particular user preference or for specialized medical diagnostic procedures.

The present invention has now been described with reference to several embodiments thereof. It will be apparent to those skilled in the art that many changes or additions can be made in the embodiments described without departing from the scope of the present invention. Thus, the scope of the present invention should not be limited to the structures described in this application, but only by the language of the claims and the equivalents of those structures.

What is claimed is:

1. An ear tip for a stethoscope for delivering sound to a canal of a human ear, the stethoscope having a pair of sound-transmitting members with distal ends, said ear tip comprising:

a central portion having attachment means for releasably attaching the ear tip to a distal end of a sound-transmitting member of the stethoscope;

a first end portion having surfaces defining an outlet, and ear contacting surfaces that are sized and shaped to afford engagement with the ear; and a second end portion having surfaces defining an outlet, and ear contacting surfaces that are sized and shaped to afford engagement with the ear;

wherein said attachment means affords releasable connection of the ear tip to the sound-transmitting member of the stethoscope in either of: a) a first orientation in which the ear contacting surfaces of the first end portion are positioned relative to the stethoscope to engage the ear, and the ear contacting surfaces of the second end portion are spaced from the ear; or b) a second orientation in which the ear contacting surfaces of the second end portion are positioned relative to the stethoscope to engage the ear, and the ear contacting surfaces of the first end portion are spaced from the ear.

2. An ear tip according to claim 1 wherein the first and second end portions each have a size, shape, and a type, and
wherein said first end portion is the same size, shape and type as the second end portion.

3. An ear tip according to claim 1 wherein the first and second end portions each have a size, shape, and a type, and
wherein said first end portion is the same shape as the second end portion.

4. An ear tip according to claim 3 wherein said first end portion has a larger size than the second end portion.

5. An ear tip according to claim 4 wherein said first end portion is the same type as the second end portion.

6. An ear tip according to claim 5 wherein the first and second end portions are constructed from materials, and
the first and second end portions are constructed from the same material.

7. An ear tip according to claim 4 wherein said first end portion is of a different type than the second end portion.

8. An ear tip according to claim 7 wherein the first and second end portions are constructed from materials, and
the second end portion is constructed from a firmer material than the material of said first end portion.

9. An ear tip according to claim 8 wherein the ear tip is adapted for use with a human ear having an auditory canal with interior surfaces and an exterior, and an exterior acoustic meatus, and
the ear contacting surfaces of the second end portion are sized and shaped to engage the interior surfaces of the auditory canal of the ear, and the ear contacting surfaces of the first end portion are sized and shaped to contact the external acoustic meatus of the exterior of the auditory canal.

10. An ear tip according to claim 9 wherein the ear tip is adapted for use with a human ear having a concha with an interior portion, a tragus and an auditory canal orifice, and
the ear contacting surfaces of the second end portion are designed to be positioned in the interior portion of the concha behind the tragus over the auditory canal orifice.

11. An ear tip according to claim 1 wherein the first and second end portions each have a size, shape, and a type, and
wherein said first end portion has a different shape than the second end portion.

12. An ear tip according to claim 11 wherein the ear contacting surface of said first end portion has a greater surface area than the ear contacting surface of said second end portion.

13. An ear tip according to claim 11 wherein said first end portion is bulbous shaped and said second end portion is mushroom shaped.

14. An ear tip according to claim 1 wherein the attachment means comprises at least one recess for engaging at least one flange on the distal end of a sound transmitting member of a stethoscope.

15. An ear tip according to claim 1 wherein, the outlet of the second portion is sized and shaped so that, in the first orientation, the distal end of the sound transmitting member is passed through the outlet of the second end portion and into the central portion.

16. An ear tip according to claim 1 wherein the ear tip is constructed from a uniform material.

* * * * *